United States Patent [19]

Conte et al.

[11] Patent Number: 5,847,247
[45] Date of Patent: *Dec. 8, 1998

[54] TERPENE-BASED SOLVENTS

[75] Inventors: Alexander J. Conte, Panama City Beach; Bobby G. Johnson, Panama City; Raymond H. Jones; Claude F. Phillips, Jr., both of Lynn Haven, all of Fla.

[73] Assignee: Arizona Chemical Company, Panama City, Fla.

[*] Notice: The term of this patent shall not extend beyond the expiration date of Pat. No. 5,723,708.

[21] Appl. No.: 618,247

[22] Filed: Mar. 18, 1996

Related U.S. Application Data

[63] Continuation-in-part of Ser. No. 227,807, Apr. 14, 1994, abandoned.

[51] Int. Cl.[6] ............................ C07C 13/00; C07C 13/32; C07C 2/76
[52] U.S. Cl. ............................... 585/20; 585/10; 585/11; 585/12; 585/16; 585/17; 585/21; 585/22; 585/23; 585/350; 585/360; 585/361; 585/362
[58] Field of Search ................................ 585/10, 11, 12, 585/16, 17, 20, 21, 22, 23, 350, 360, 361, 362

[56] References Cited

U.S. PATENT DOCUMENTS

| | | |
|---|---|---|
| 1,691,067 | 11/1928 | Humphrey . |
| 1,691,068 | 11/1928 | Humphrey . |
| 1,793,220 | 2/1931 | Humphrey . |
| 2,249,112 | 7/1941 | Carmody . |
| 2,393,915 | 1/1946 | Kirkpatrick . |
| 2,543,092 | 2/1951 | Bondhus et al. . |
| 2,792,436 | 5/1957 | Kroeper et al. . |
| 2,831,037 | 4/1958 | Schmerling . |
| 2,913,443 | 11/1959 | Edmonds, Jr. . |
| 3,270,075 | 8/1966 | Derfer et al. . |
| 3,280,207 | 10/1966 | Liquori et al. . |
| 3,297,673 | 1/1967 | Sellers, Jr. et al. . |
| 3,401,136 | 9/1968 | Sellers, Jr. . |
| 3,413,246 | 11/1968 | Weymann et al. . |
| 3,415,769 | 12/1968 | Todd et al. . |
| 3,415,893 | 12/1968 | Sellers, Jr. et al. . |
| 3,466,267 | 9/1969 | Derfer . |
| 3,502,769 | 3/1970 | Fukuhara . |
| 3,622,550 | 11/1971 | Patellis et al. . |
| 3,642,928 | 2/1972 | Davis . |
| 3,696,164 | 10/1972 | Davis . |
| 3,700,746 | 10/1972 | Takacs . |
| 3,700,747 | 10/1972 | Takacs . |
| 3,737,418 | 6/1973 | Ruckel et al. . |
| 3,761,457 | 9/1973 | Arlt, Jr. et al. . |
| 3,931,077 | 1/1976 | Uchigaki et al. . |
| 4,052,549 | 10/1977 | Booth . |
| 4,165,301 | 8/1979 | Weigers et al. . |
| 4,170,576 | 10/1979 | Hall et al. . |
| 4,399,249 | 8/1983 | Bildusas . |
| 4,922,047 | 5/1990 | Chen . |
| 5,085,849 | 2/1992 | Sampson et al. . |
| 5,092,907 | 3/1992 | Riblet et al. . |
| 5,112,516 | 5/1992 | Koetzle . |

FOREIGN PATENT DOCUMENTS

WO 91/00893  1/1991  WIPO .

OTHER PUBLICATIONS

J.J. Ritter, J.G. Sharekin. 1940. "Acid–polymerized Dipinene. I. Dehydrogenation, & II. Identification of the Dehydrogenate.", J. Amer. Chem. Soc. 62:1508–1511. no month available.

N.K. Roy, B.S. Rathore, G.B. Butler. 1972. "Structural Studies on α–pinene Dimers.", J. Indian Chem. Soc. 49:1221–1238. no month available.

R.S. Gallagher. Mar./Apr. 1993. "The status of terpene cleaners as replacements for restricted solvents in industrial metal cleaning applications.", Naval Stores Review. no month available.

*Primary Examiner*—Elizabeth D Wood
*Attorney, Agent, or Firm*—Luedeka, Neely & Graham, P.C.

[57] ABSTRACT

The specification discloses terpene-based solvent compositions which comprise diterpenes as a major component and a minor amount of monoterpenes. The mixtures exhibit solvent properties similar to monoterpenes but have flash points high enough to be classified as combustible rather than flammable materials.

47 Claims, No Drawings

TERPENE-BASED SOLVENTS

This application is a continuation-in-part of application Ser. No. 08/227,807, filed on Mar. 14, 1994, now abandoned.

FIELD OF THE INVENTION

The present invention is directed to terpene-based solvents which exhibit solvent properties similar to those of monoterpenes but with decreased flammability.

BACKGROUND

Monoterpenes are widely used as solvents and possess many desirable properties. However, monoterpenes have a relatively low flash point and thus are quite flammable. Higher molecular weight terpenes, such as diterpenes exhibit a much higher flash point than monoterpenes, however, the solvent properties of diterpenes are inferior to those of the monoterpenes for many applications.

Methods for decreasing the flammability of monoterpene-based solvents include halogenating the terpenes or adding one or more flame retardants to the monoterpene solvents. Flame retardants, while useful for decreasing the flammability of the terpene solvents, increase the cost of such solvents and may result in the release of halogenated organic compounds to the atmosphere upon combustion of the solvent as well as a decrease in desirable solvent properties. Furthermore, there is increasing pressure from the Environmental Protection Agency and other environmental groups to reduce the use of halogenated solvents and solvents containing halogenated compounds.

Another method for increasing the flash point of monoterpene is to prepare a mixture of terpene (about 21 wt. %) and aliphatic hydrocarbons (about 79 wt. %) having an average molecular weight in the range of about 200 $M_w$. One such solvent material is a mixture of orange oils (limonene), mineral spirits and anti-oxidants and is commercially available from Pronatur Products Ltd. of Bootle, Liverpool, England under the trade name PRONATUR. Despite its relatively high flash point (66° to 69° C.), PRONATUR solvent may not be an acceptable solvent for many applications due to its high mineral oil content and inherent toxicity. Mineral oil-based solvents have also lost favor with environmental groups recently due to their lack of biodegradeability.

It is therefore an object of the present invention to provide a relatively high flash point terpene-based solvent composition having solvency properties approaching those of monoterpenes.

It is another object of the invention to provide a solvent composition derived from non-toxic ingredients.

Another object of the invention is to provide a method for increasing the flash point of terpene-based solvents.

A further object of the invention is to provide a method for preparing high flash point terpene-based solvents derived from naturally occurring monoterpenes.

Still another object of the invention is to provide a terpene solvent which exhibits solvent properties similar to those of monoterpenes but which is classified as a combustible rather than a flammable material.

THE INVENTION

With regard to the above and other objects, the present invention provides a terpene-based solvent composition which comprises a mixture containing from about 20 to about 35 wt. % monoterpene and from about 65 to about 80 wt. % diterpene, preferably from about 25 to about 30 wt. % monoterpene and from about 70 to about 75 wt. % diterpene.

Terpene-based solvent compositions according to the invention exhibit a flash point above about 60° C. and therefore may be classified as combustible rather than flammable. Surprisingly, the compositions exhibit solvency properties which are similar to monoterpenes, despite the fact that the diterpene is the major component. Thus in terms of the Kauri-butanol (Kb) value, terpene-based solvent compositions according to the invention exhibit a Kb value more like that of a monoterpene than a diterpene, despite the fact that the composition is predominately diterpene.

In a related aspect, the invention provides a process for making terpene-based solvent compositions. The process comprises preparing a mixture of an inorganic acid and at least one monoterpene having the molecular formula $C_{10}H_{16}$ and dimerizing from about 65 to about 80 wt. % of the monoterpene in the mixture at a temperature which is sufficient to provide a solvent composition containing from about 20 to about 35 wt. % monoterpene. The product from the dimerization reaction, when conducted according to the process disclosed herein, contains monomeric by-products and is substantially free of higher terpene oligomers having molecular formulas greater than $C_{20}H_{32}$. By "substantially free", it is meant that higher terpene oligomers are present in the compositions in amounts less than about 15 wt. % and preferably less than about 5 wt. %. The monomeric by-products are terpene materials such as p-cymene, α-terpinene, γ-terpinene and isoterpinolene. The reaction product from the dimerization reaction may be used as is without purification or removal of the terpene by-products.

Preferred monoterpenes which may be used in the reaction mixture are the naturally occurring monoterpenes selected from the group consisting of α-pinene, β-pinene, d-limonene, cineoles, mixtures of two or more of the foregoing or other monoterpenes containing at least one double bond. Particularly preferred monoterpenes have the molecular formula $C_{10}H_{16}$ with α-pinene being the most preferred monoterpene.

In the first step of the dimerization reaction, a monoterpene of the formula $C_{10}H_{16}$ is mixed with an inorganic acid. The mixture preferably contains from about 0.5 to about 1.5 parts of monoterpene, preferably about 1.0 part of monoterpene, and from about 0.2 to about 1.0 parts by weight of an inorganic acid, preferably about 0.6 parts acid. It is particularly preferred to use a ratio of monoterpene to inorganic acid which is greater than 1.0.

The inorganic acid may be selected from the group consisting of phosphoric acid, sulfuric acid and other inorganic phosphorus-containing acids. Although a preferred acid is a polyprotic acid, monoprotic acids may also be used. The acid concentration may vary widely provided the concentration does not adversely affect the rate of the dimerization reaction. Preferred acid concentrations range from about 75 to about 85 wt. %.

The dimerization reaction of the monoterpene may be conducted at a temperature in the range of from about 25° to about 120° C. It is preferred to conduct the reaction at an elevated temperature in order to advance the reaction as quickly as possible. A particularly preferred reaction temperature is in the range of from about 90° to about 120° C.

By controlling the reaction temperature and acid concentration, the extent of the reaction may be adjusted so that the reaction product contains the desired amount of diterpene component directly. In order to determine the extent of reaction, a 100° C. non-volatiles test is used. The 100° C. non-volatiles test is run by placing one grain of reaction mass on a two inch diameter flat bottom aluminum pan. The pan containing the sample is then placed on a 100° C. steam plate for one hour and the percent non-volatiles is calculated by dividing the final weight of the sample by the initial weight. In the alternative, the refractive index of the reaction mass may be used to determine the extent of reaction. The rate of change of the refractive index or weight loss of the reaction mass declines as the dimerization progresses. Accordingly, when the rate of change of the refractive index or weight loss is near zero, the reaction is substantially complete.

During the dimerization reaction, a non-oxidizing inert gas atmosphere is preferably used. Suitable inert gases may be selected from nitrogen, argon, carbon dioxide and the like and may be used to reduce oxidation of the reactants and products during the reaction. Oxidation products tend to discolor the reaction products to an undesirable degree.

The diterpene components of the solvent compositions of the invention also contain at least one double bond, and are preferably derived from the monoterpenes in the compositions. Preferred diterpenes have the molecular formula $C_{20}H_{32}$ and include tricyclic structures, bicyclic structures and/or monocyclic structures.

The reaction mixture of monoterpene and inorganic acid may optionally include a cationic or anionic surfactant. Addition of a surfactant such as IGEPAL CO-630 which is commercially available from Rhone-Poulenc, GAF Chemicals Group of New Jersey, may be used to increase the reaction rate. However, the separation of the inorganic material from the organic material in the reaction product may be simpler without the use of a surfactant.

During the dimerization reaction, an organic layer containing monoterpene, diterpene and monomeric byproducts and an aqueous layer containing the inorganic acid are formed. The aqueous layer may be separated from the organic layer and recycled for subsequent dimerization reactions. Separation techniques which may be used include centrifugation, decantation, distillation, extraction, adsorption and the like.

The resulting organic layer containing unreacted monoterpene, diterpene and monomeric by-products may be used as is as a solvent or may be further purified to remove the monomeric by-products. Purification techniques include distillation, extraction and the like.

In the alternative, the solvent compositions of this invention may be prepared by combining the monoterpene component and the diterpene component in the desired proportions by any known formulation technique. Or, the reaction products described above may be adjusted by adding monoterpene or diterpene to obtain the desired proportions of monoterpene and diterpene components.

The following examples are given to illustrate various aspects of the present invention and are not intended to limit the invention in any way.

EXAMPLE 1

A monoterpene/diterpene mixture was made by combining α-pinene (ACINTENE A ALPHA PINENE, commercially available from Arizona Chemical Company of Panama City, Fla., ACINTENE is a registered trademark of Arizona Chemical Company) with phosphoric acid (85 wt. %, 0.6 parts by weight, 180 grams) in a flask fitted with a thermometer, agitator and nitrogen purge system. The acid was pre-heated to 90° C. and the α-pinene (1.0 part by weight, 300 grams) was added over a period of two hours to the acid while controlling the mixture temperature during the addition to within two degrees of 90° C. The mixture was then held at 90° C. for 21 hours while stirring the mixture.

During the 21 hour hold period, samples were removed periodically from the reaction mass for analysis. Each sample was washed with dilute potassium carbonate to quench the reaction. The extent of dimerization was determined by the use of a 100° C. non-volatiles test. The non-volatiles test was conducted by placing one gram of the reaction mass sample in a two inch diameter flat bottom aluminum pan. The sample was then placed on a 100° C. steam plate for one hour and the percent non-volatiles was determined as the percentage of weight loss in the sample based on the initial weight of sample. The extent of reaction versus reaction time is given in Table 1.

TABLE 1

| Reaction time (hours from point all α-pinene added to flask) | 100° C. Non-volatiles (wt. %) |
|---|---|
| 2 | 27 |
| 4 | 37 |
| 10 | 64 |
| 21 | 74 |

After 23 hours of reaction time, the condensation reaction was substantially complete. At this point the agitator was stopped and the bottom aqueous layer containing phosphoric acid was separated from the organic layer. The organic layer was washed once with dilute potassium carbonate and twice with distilled water.

EXAMPLE 2

The procedure of Example 1 was repeated on a larger scale using 1588 kg of ACINTENE A and 953 kg of 85 wt. % phosphoric acid. Analytical properties of the reaction product after 24 hours reaction time are given in Table 2. In determining the properties of the reaction product the following testing procedures were used:

Volatile Organic Compounds (VOC) - ASTM D2369-81
Flash Point of Mixture - ASTM D3278-87, D3828-81
Gardner Color - ASTM D1544-80 on a scale from 1–18 wherein 18 is darkest and 1 is lightest.
Kauri-butanol value (Kb) - determined by amount of substance which will produce enough turbidity in a butanol solution of Kauri resin to obscure newsprint. The higher the value, the higher the solvency of the substance for polar materials. Conversely, the lower the value, the higher the solvency of the substance for nonpolar materials.

TABLE 2

| ANALYTICAL PROPERTIES | Value |
|---|---|
| Gardner Color (ASTM D1544-80) | 3– |
| Kauri-butanol value (Kb) (ASTM D1133-86) | 49 |
| Volatile Organic Compounds (VOC) (EPA Method 24) | 62% |
| Volatiles (230° C. at 0.15 mm Hg) | >99% |
| Flash Point (setaflash closed cup tester) | 63° C. |
| Viscosity (25° C. Brookfield, LVT Viscometer #2 spindle) | 13 cp |
| Odor | Woody |

As illustrated by the high flash point, the reaction product may be classified as combustible rather than flammable because its flash point is above 60° C.

Using gel permeation chromatography, it was determined that the diterpene component of the reaction product contained about 2.4 wt. % trimer plus oligomer. Gas chromatography (GLC) analysis indicated that the terpene dimer constituent of the reaction product was a complex mixture of at least 50 components. GLC/mass spectrophotometric analysis of the diterpene indicated that the components of the diterpene constituent all have a molecular weight of 272 corresponding to the formula $C_{20}H_{32}$ which results from the condensation of two molecules of α-pinene.

GLC analysis also indicated that the a-pinene may rearrange to other monoterpene and monomeric by-products during the dimerization reaction, all of which have $C_{10}H_{14}$, $C_{10}H_{16}$ and $C_{10}H_{18}$ molecular formulas.

At the end of the 24 hour reaction period, the non-volatiles content using the 100° non-volatiles test was 69 percent by weight. Thus the ratio of monoterpene to diterpene in the reaction product was 31:69 by weight.

EXAMPLE 3

The process conditions in Example 1 were repeated in two additional reaction experiments using 85 wt. % phosphoric acid at 100° C. In the first reaction, after 23 hours, the non-volatiles content of the reaction product was 67 wt. %. In the second reaction, after 22 hours, the non-volatiles content of the reaction product was 69 wt. %.

As compared to Example 1, the dimerization reaction conducted at 100° C. may result in a reaction product containing less diterpene than a reaction product obtained by conducting the reaction at a temperature of 90° C.

EXAMPLE 4

In the following tables, various blends of monoterpenes and diterpenes and the properties of the blends are illustrated.

TABLE 3

| Monoterpene | Diterpene | Monoterpene Flash Point (°C.) | Monoterpene/Diterpene Blend Ratio | Monoterpene/Diterpene Blend Flash Point (°C.) | Blend Name |
|---|---|---|---|---|---|
| ACINTENE P-AC[1] | DC-2203[2] | 35 | 30/70 | 47 | — |
| ACINTENE P-AC | CC-2248[3] | 35 | 30/70 | 47 | — |
| MGL[4] | DC-2203 | 49 | 30/70 | 63 | — |
| MGL | CC-2248 | 49 | 30/70 | 63 | XC-2289 |
| ACINTENE A[5] | DC-2203 | 35 | 30/70 | 49 | — |
| ACINTENE A | CC-2248 | 35 | 30/70 | 49 | — |
| ACINTENE DP-738[6] | DC-2203 | 43 | 30/70 | 59 | — |
| ACINTENE DP-738 | CC-2248 | 43 | 30/70 | 59 | — |
| ACINTENE DP-738 | CC-2248 | 43 | 25/75 | 61 | — |
| ACINTENE DP-738 | CC-2248 | 43 | 20/80 | 61 | — |
| ACINTENE AC-P[7] | DC-2203 | 39 | 30/70 | 57 | — |
| ACINTENE AC-P | CC-2248 | 39 | 30/70 | 57 | — |
| ACINTENE AC-P | CC-2248 | 39 | 25/75 | 59 | — |
| ACINTENE AC-P | CC-2248 | 39 | 20/80 | 59 | — |
| ACINTENE LS-160D[8] | CC-2248 | 43 | 25/75 | 63 | XC-2290 |
| ACINTENE LS-160D | DC-2203 | 43 | 25/75 | 63 | — |
| ACINTENE LS-160D | XC-2283[9] | 43 | 25/75 | 63 | — |
| MGL | XC-2283 | 49 | 30/70 | 63/64 | XC-2293 |
| XC-2285[10] | XC-2283 | 48 | ~25/75 | 63 | XC-2284[11] |
| XC-2285 | CC-2248 | 48 | 30/70 | 63 | XC-2315 |

[1]ACINTENE P-AC - a colorless liquid containing about 81 wt. % α-pinene and about 14 wt. % camphene as determined by gas-liquid chromatographic analysis available from Arizona Chemical Company of Panama City, Florida.
[2]D- 2203 - a diterpene from α-pinene which was high in triterpenes.
[3]CC-2248 - a diterpene derived from ZONATAC resins (light oils) commercially available from Arizona Chemical Company of Panama City, Florida.
[4]MGL - Monomer grade limonene
[5]ACINTENE A - a colorless liquid containing about 95 wt. % α-pinene as determined by gas-liquid chromatographic analysis available from Arizona Chemical Company of Panama City, Florida.
[6]ACINTENE DP 738 - a colorless liquid containing about 17 wt. % α-pinene, about 16 wt. % 1,4-cineole, about 24 wt. % dipentene or limonene, about 11 wt. % 1,8-cineole and about 12 wt. % terpinolene as determined by gas-liquid chromatographic analysis available from Arizona Chemical Company of Panama City, Florida.
[7]ACINTENE AC-P - a colorless liquid containing about 32 wt. % α-pinene, about 13 wt. % 1,4-cineole, about 19 wt. % dipentene or limonene, about 8 wt. % camphene and about 9 wt. % terpinolene as determined by gas-liquid chromatographic analysis available from Arizona Chemical Company of Panama City, Florida.
[8]ACINTENE LS-160 D - a colorless liquid containing about 94 wt. % ACINTENE DP 738 and about 6 wt. % of an odor mask as determined by gas-liquid chromatographic analysis available from Arizona Chemical Company of Panama City, Florida.
[9]XC-2283 - a diterpene prepared from α-pinene which was low in triterpenes.
[10]XC-2285 - a monoterpene mixture from the dimerization product of α-pinene.
[11]XC-2284 - a reaction product mixture from the dimerization of α-pinene.

As illustrated by the examples in the foregoing table, a terpene solvent with a flash point above about 60° C. may be prepared by mixing a monoterpene having a flash point above about 40° C. with a diterpene in the ratios indicated in the table.

The properties of blends identified in Table 3 are further illustrated in Table 4 below.

TABLE 4

| Analysis | XC-2289 | XC-2290 | XC-2284 | XC-2293 | XC-2315 |
|---|---|---|---|---|---|
| Gardner Color | 1+ | 1+ | 3− | 3 | 1+ |
| Flash Point (°C.) | 63 | 62 | 63 | 64 | 63 |
| Viscosity at 25° C. (cp) | 11.5 | 25 | 10.5 | 7.5 | 16 |
| Nonvolatiles (steam plate) (wt. %) | 67.3 | 71.9 | 71.1 | 66.8 | 68.5 |
| Nonvolatiles (230° C. High vacuum) (wt. %) | 3.8 | 4.7 | 0.3 | 0.5 | 3.8 |
| Kauri-butanol value (Kb) | 100 | 148 | 49 | 48 | 100 |
| Odor | citrus | pine | pine | citrus | pine |
| VOC's (EPA Method 24) (wt. %) | 62.9 | 58.7 | 61.8 | 69.3 | 64.4 |

TABLE 4-continued

| Analysis | XC-2289 | XC-2290 | XC-2284 | XC-2293 | XC-2315 |
|---|---|---|---|---|---|
| Surface Tension (dynes/cm) | 34.4 | 35.0 | 33.4 | 33.0 | 34.1 |
| Hydrogen Bonding Group | Poor[1] | Poor to Moderate[2] | Poor[1] | Poor[1] | Poor[1] |
| Evaporation Rate[3] (n-butyl acetate = 1) | <0.01 | <0.01 | <0.01 | <0.01 | <0.01 |

[1]Hydrocarbons are in this group.
[2]Contains 5–10% by weight ethers, which are moderate in hydrogen bonding.
[3]Relative to 1.0 for n-butyl acetate (ASTM D-3539-76). These values are projected. Relative evaporation rate is calculated from the 90 weight percent evaporation time for the test solvent and for n-butyl acetate.

As illustrated by the foregoing examples, solvent compositions containing from about 25 to about 30 wt. % monoterpene and from about 70 to about 75 wt. % diterpene may be prepared which have flash points above about 60° C. and solvency properties as determined by the Kb values ranging from about 48 to about 148. Hence, the solvent properties may also be tailored to vary from less polar (low Kb values) to more polar (high Kb values) depending on the particular solvent application.

EXAMPLE 5

In the following Table 5, the solvency of various monoterpene/diterpene compositions are compared to the solvency of the individual components of the compositions.

TABLE 5

| Monoterpene | | Diterpene | | Monoterpene/Diterpene | | Blend | |
|---|---|---|---|---|---|---|---|
| Name | Kb | Name | Kb | Ratio | Kb | Name | |
| XC-2285 | 61 | XC-2283 | 95 | ~25/75 | 49 | XC-2284 | |
| XC-2285 | 61 | CC-2248 | 41 | 30/70 | 100 | XC-2315 | |
| MGL | 75 | CC-2248 | 41 | 30/70 | 100 | XC-2289 | |
| ACINTENE LS-160D | 100 | CC-2248 | 41 | 25/75 | 148 | XC-2290 | |
| MGL | 75 | XC-2283 | 95 | 30/70 | 48 | XC-2293 | |

As illustrated by the examples in Table 5, the polarity (Kb value) of a monoterpene/diterpene blend may be higher or lower than that of diterpene from which the blend is derived. While not desiring to be bound by theoretical considerations, it is believed that a cosolvent effect may be occurring which renders the mixture of monoterpene/diterpene more polar than the diterpene when a less polar diterpene is used in the mixture and less polar than the diterpene when a more polar diterpene is used in the mixture. Accordingly, the cosolvency effect may be used to tailor the polarity of the solvent compositions as illustrated above to obtain a material which is suitable for more polar or less polar solvent applications as the need arises.

Having thus described various features, aspects and advantages of the preferred known embodiments of the present invention, it will be recognized by those of ordinary skill that numerous variations, modifications and substitutions of the same may be made within the spirit and scope of the appended claims.

What is claimed is:

1. A terpene-based solvent composition consisting essentially of a terpene mixture containing from about 20 to about 35 wt. % monoterpene and from about 65 to about 80 wt. % diterpene.

2. The solvent composition of claim 1 having a Kauri-butanol (Kb) value within the range of from about 50 to about 150.

3. The solvent composition of claim 1 wherein the terpene mixture contains from about 25 to about 30 wt. % monoterpene and from about 70 to about 75 wt. % diterpene.

4. The solvent composition claim 3 wherein the terpene mixture is a dimerization reaction product of α-pinene.

5. The solvent composition of claim 4 wherein the monoterpene comprises a mixture of p-cymene, α-terpinene, γ-terpinene, isoterpinolene, and other monoterpene byproducts from the dimerization of α-pinene.

6. The solvent composition of claim 3 wherein the monoterpene is d-limonene.

7. The solvent composition of claim 3 wherein the monoterpene comprises a mixture of α-pinene, cineoles, dipentene and terpinolene.

8. The solvent composition claim 3 wherein the diterpene is a dimerization reaction product of α-pinene.

9. The solvent composition of claim 3 wherein the terpene mixture is a dimerization reaction product of d-limonene.

10. The solvent composition of claim 3 wherein the diterpene is a distillation product obtained from the polymerization reaction of a mixture of dipentene and styrene monomer.

11. A process for preparing a terpene-based solvent composition comprising:
    providing a reaction mixture which comprises an inorganic acid and at least one monoterpene having the molecular formula $C_{10}H_{16}$; and
    dimerizing the mixture at a temperature and under conditions which are sufficient to produce a solvent composition consisting essentially of from about 20 to about 35 wt. % monoterpene and from about 65 to about 80 wt. % diterpene and having a flash point of at least about 60° C.

12. The process of claim 11 wherein the solvent composition is substantially free of higher terpene oligomers having molecular formulas greater than $C_{20}H_{32}$.

13. The process of claim 11 wherein the dimerization temperature is within the range of from about 90° to about 120° C.

14. The process of claim 11 wherein the solvent composition thus prepared has a Kauri-butanol (Kb) value within the range of from about 50 to about 150.

15. The process of claim 11 wherein the solvent composition contains from about 25 to about 30 wt. % monoterpene and from about 70 to about 75 wt. % diterpene.

16. The process of claim 15 wherein the monoterpene in the reaction mixture comprises a mixture of α-pinene, β-pinene and cineoles.

17. The process of claim 11 wherein the monoterpene in the reaction mixture comprises of a mixture of α-pinene, β-pinene and cineoles.

18. The process of claim 11 wherein the monoterpene in the reaction mixture is d-limonene.

19. The process of claim 11 wherein the monoterpene in the reaction mixture is α-pinene.

20. The process of claim 11 wherein the reaction mixture further comprises a surface active agent.

21. The process of claim 11 wherein the reaction mixture is 1.0 part by weight monoterpene and at least 0.3 parts by weight inorganic acid.

22. The process of claim 21 wherein the inorganic acid is phosphoric acid.

23. The process of claim 11 wherein the inorganic acid is phosphoric acid.

24. The process of claim 11 further comprising conducting the dimerization step under an inert gas atmosphere. product substantially free of higher terpene oligomers having molecular formulas greater than $C_{20}H_{32}$ and comprising from about 20 to about 35 wt. % monoterpene.

25. A method for making a terpene-based solvent composition which consists essentially of:
providing a reaction mixture comprising an inorganic acid and at least one monoterpene having the molecular formula $C_{10}H_{16}$; and
reacting the monoterpene/acid mixture at a temperature in the range of from 90° to about 120° C. and under conditions sufficient to produce a reaction product substantially free of higher terpene oligomers having molecular formulas greater than $C_{20}H_{32}$ and consisting essentially of from about 20 to about 35 wt. % monoterpene and from about 65 to about 80 wt. % diterpene.

26. The method of claim 25 wherein the solvent composition contains from about 25 to about 30 wt. % monoterpene and from about 70 to about 75 wt. % diterpene.

27. The method of claim 26 wherein the monoterpene in the reaction mixture comprises a mixture of α-pinene, β-pinene and cineoles.

28. The method of claim 26 wherein the monoterpene in the reaction mixture is d-limonene.

29. The method of claim 26 wherein the monoterpene in the reaction mixture is α-pinene.

30. The method of claim 25 wherein the reaction mixture is 1.0 part by weight monoterpene and at least 0.3 parts by weight inorganic acid.

31. The method of claim 25 wherein the inorganic acid is phosphoric acid.

32. A method for making a terpene-based solvent composition having predetermined solvency properties in terms of a Kauri-butanol (Kb) value which consists essentially of mixing from about 20 to about 35 wt. % monoterpene having a first Kb value with from about 65 to about 80 wt. % diterpene having a second Kb value wherein the Kb value of the resulting mixture is within the range of from about 40 to about 150 and the flash point is above about 60° C.

33. The method of claim 32 wherein the solvent composition comprises from about 25 to about 30 wt. % monoterpene and from about 70 to about 75 wt. % diterpene.

34. The method of claim 32 wherein the first Kb value is within the range of from about 55 to about 80, the second Kb value is within the range of from about 80 to about 100 and the solvent composition has a Kb value within the range of from about 40 to about 60.

35. The method of claim 32 wherein the first Kb value is within the range of from about 60 to about 100, the second Kb value is within the range of from about 30 to about 50 and the solvent composition has a Kb value within the range of from about 100 to about 150.

36. The method of claim 32 further comprising selecting a solvent composition having a Kb value lower than the first and second Kb values and mixing a monoterpene having a Kb value higher than the Kb value of the mixture with a diterpene having a Kb value higher than the Kb value of the mixture to obtain the lower Kb value of the solvent composition.

37. The method of claim 35 wherein the first Kb value is within the range of from about 55 to about 80, the second Kb value is within the range of from about 60 to about 100 and the solvent composition has a Kb value within the range of from about 30 to about 50.

38. The method of claim 32 further comprising selecting a solvent composition having a Kb value higher than the first and second Kb values of the monoterpene and diterpene and mixing a monoterpene having a Kb value lower than the Kb value of the mixture with a diterpene having a Kb value lower than the Kb value of the mixture to obtain the higher Kb value of the solvent composition.

39. The method of claim 37 wherein the first Kb value is within the range of from about 55 to about 95, the second Kb value is within the range of from about 35 to about 55 and the solvent composition has a Kb value within the range of from about 100 to about 150.

40. The method of claim 22 wherein the monoterpene has a flash point of at least about 40° C.

41. The method of claim 25 wherein the monoterpene has a flash point of at least about 40° C.

42. The process of claim 11 wherein the monoterpene has a flash point of at least about 40° C.

43. The solvent composition of claim 1 wherein the monoterpene has a flash point of at least about 40° C.

44. The method of claim 32 wherein the flash point of the mixture is at least about 60° C.

45. The method of claim 25 wherein the flash point of the reaction product is at least about 60° C.

46. The solvent composition of claim 1 wherein the flash point of the mixture is at least about 60° C.

47. A composition which consists essentially of from about 20 to about 35 wt. % monoterpene and from about 65 to about 80 wt. % diterpene and having a flash point of at least about 60° C. and a Kb value in the range of from about 50 to about 150.

* * * * *

UNITED STATES PATENT AND TRADEMARK OFFICE
CERTIFICATE OF CORRECTION

PATENT NO.   : 5,847,247
DATED        : December 8, 1998
INVENTOR(S)  : Alexander J. Conte, Bobby G. Johnson, Raymond H. Jones and Claude F. Phillips, Jr.

It is certified that error appears in the above-identified patent and that said Letters Patent is hereby corrected as shown below:

Column 9, Claim 24, line 3., delete "product substantially free of higher terpene oligomers having molecular formulas greater than $C_{20}H_{32}$ and comprising from about 20 to about 35 wt. % monoterpene."

Signed and Sealed this

Twenty-seventh Day of April, 1999

Attest:

Q. TODD DICKINSON

*Attesting Officer*            *Acting Commissioner of Patents and Trademarks*

UNITED STATES PATENT AND TRADEMARK OFFICE
CERTIFICATE OF CORRECTION

PATENT NO. : 5,847,247
DATED : December 8, 1998
INVENTOR(S) : Conte, et. al.

It is certified that error appears in the above-identified patent and that said Letters Patent is hereby corrected as shown below:

Title page, item [*], delete "5,723,708" and insert --5,723,709--.

Signed and Sealed this

Eighth Day of February, 2000

Attest:

Q. TODD DICKINSON

Attesting Officer

Commissioner of Patents and Trademarks